(12) United States Patent
Ogura

(10) Patent No.: US 9,247,868 B2
(45) Date of Patent: Feb. 2, 2016

(54) OPHTHALMOLOGIC APPARATUS AND CONTROL METHOD OF THE SAME

(71) Applicant: CANON KABUSHIKI KAISHA, Tokyo (JP)

(72) Inventor: Hiraku Ogura, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/572,563

(22) Filed: Dec. 16, 2014

(65) Prior Publication Data

US 2015/0173601 A1 Jun. 25, 2015

(30) Foreign Application Priority Data

Dec. 19, 2013 (JP) .................................. 2013-262760

(51) Int. Cl.
*A61B 3/14* (2006.01)
*A61B 3/00* (2006.01)
*A61B 3/117* (2006.01)

(52) U.S. Cl.
CPC ............... *A61B 3/0075* (2013.01); *A61B 3/117* (2013.01); *A61B 3/14* (2013.01)

(58) Field of Classification Search
CPC .......... A61B 3/14; A61B 3/0075; A61B 3/12; A61B 3/117; A61B 3/13; A61B 3/00
USPC .................................. 351/245, 206, 205, 208
See application file for complete search history.

(56) References Cited

U.S. PATENT DOCUMENTS

| 8,770,756 B2 * | 7/2014 | Dobashi ............... | A61B 3/0075 351/208 |
| 8,845,102 B2 * | 9/2014 | Inoue .................... | A61B 3/0075 351/208 |
| 9,028,066 B2 * | 5/2015 | Akiba .................. | A61B 3/0075 351/208 |
| 2009/0079939 A1 | 3/2009 | Mimura | |
| 2012/0218520 A1 | 8/2012 | Inoue | |

FOREIGN PATENT DOCUMENTS

| JP | 2002369799 A | 12/2002 |
| JP | 2009056247 A | 3/2009 |

* cited by examiner

*Primary Examiner* — Hung Dang
(74) *Attorney, Agent, or Firm* — Canon USA, Inc. IP Division

(57) ABSTRACT

An ophthalmologic apparatus includes: a position control unit configured to control a position changing unit which changes a position of an examination unit, such that fine movement driving of the examination unit is performed in a case where a tilt angle of the operating member is smaller than a first angle, and coarse movement driving of the examination unit is performed in a case where the tilt angle of the operating member is equal to or greater than the first angle; and an angle control unit configured to control an angle changing unit which changes the angle of the operating member such that the tilt angle of the operating member is automatically changed to a second angle which is smaller than the first angle, in accordance with a change from the coarse movement to the fine movement.

16 Claims, 11 Drawing Sheets

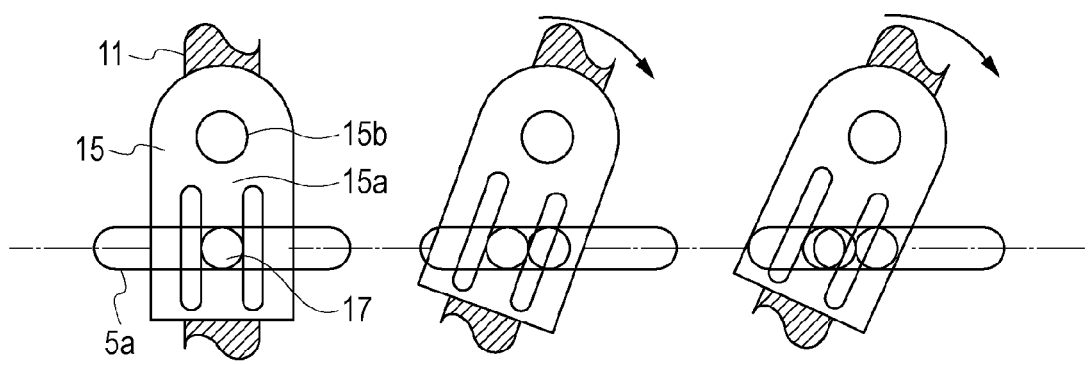

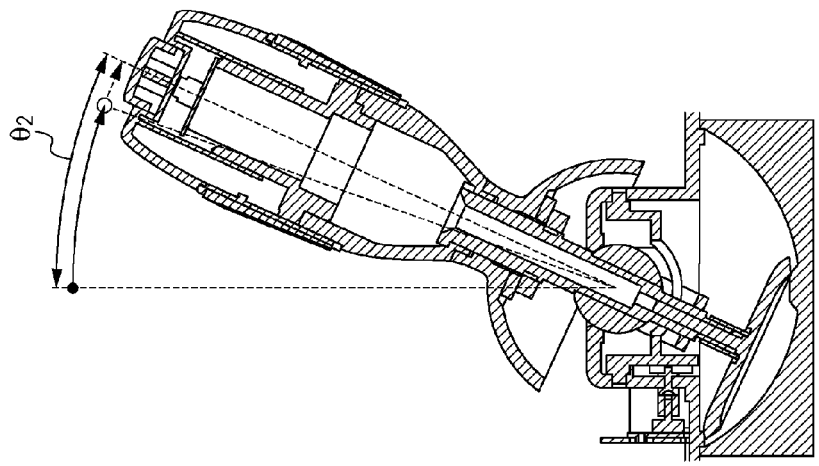
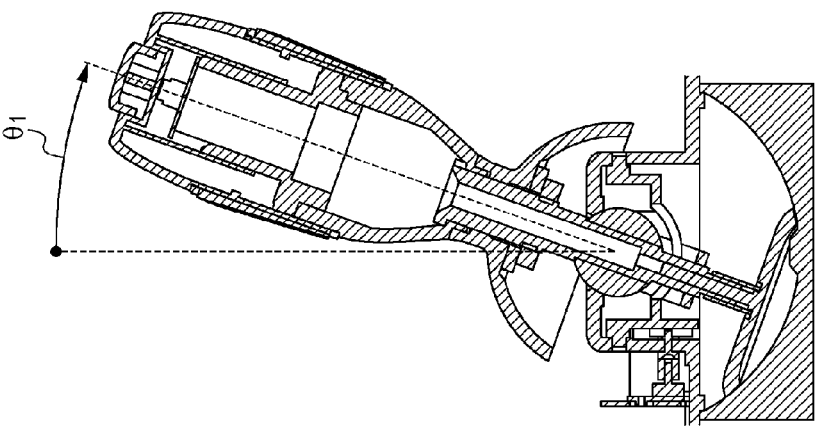
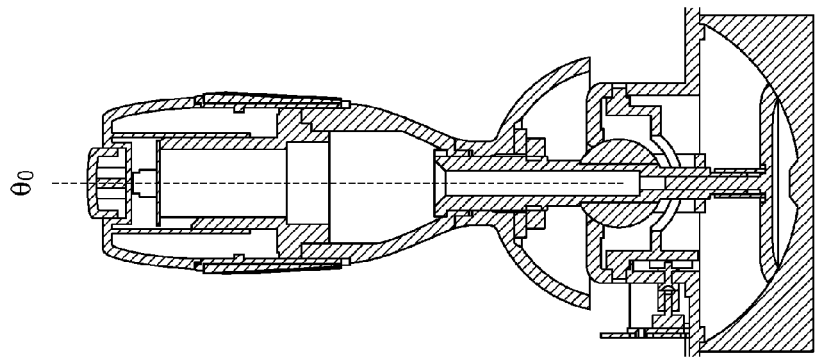

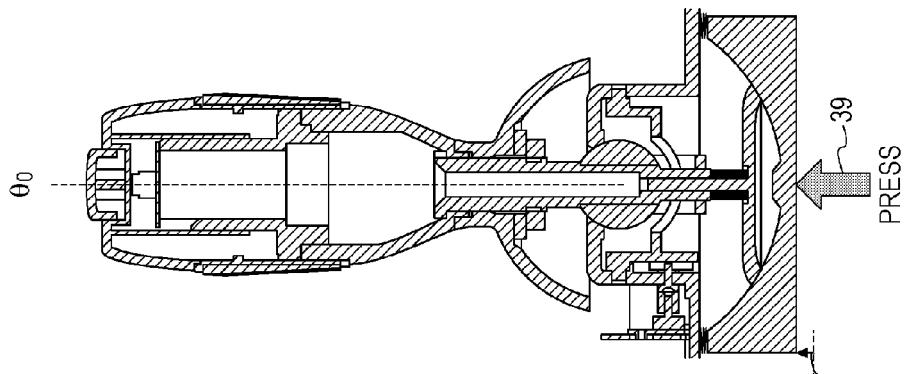
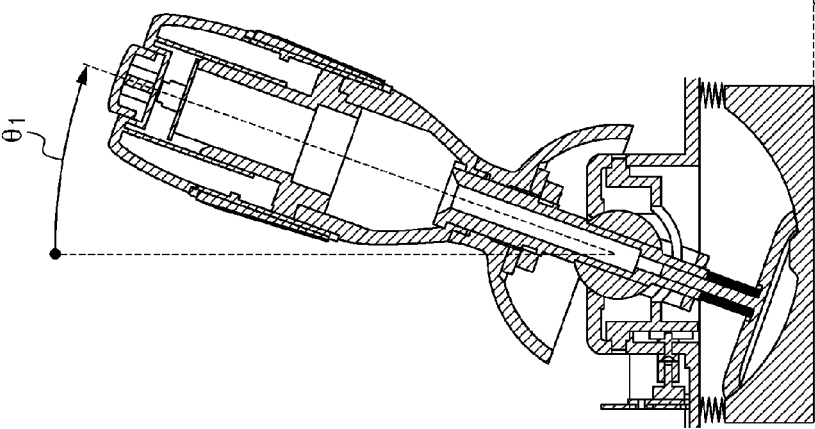
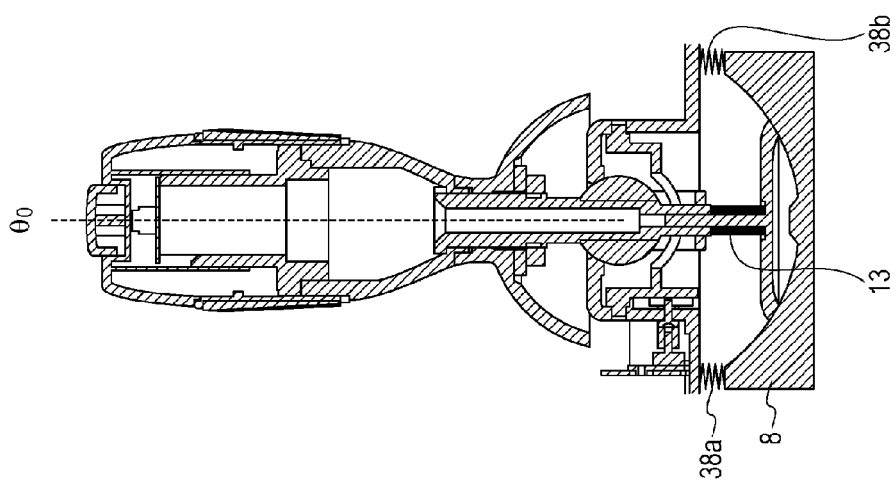

OPHTHALMOLOGIC APPARATUS AND CONTROL METHOD OF THE SAME

BACKGROUND OF THE INVENTION

1. Field of the Invention

The present invention(s) relate to at least one ophthalmologic apparatus which examines an eye to be examined.

2. Description of the Related Art

Japanese Patent Laid-Open No. 2002-369799 discloses an ophthalmologic apparatus regarding an ophthalmologic apparatus which requires positioning as to an eye to be examined (e.g., auto refractometer or fundus camera), in which examiner manipulations using a joystick or trackball or the like are electrically detected, and an examination unit having a measurement optical system and so forth is driven based on the detection results.

This ophthalmologic apparatus switches driving control of the examination unit between position control and speed control, in accordance of the inclination angle of an electric joystick. That is to say, position control (control to move the examination unit by a moving amount corresponding to the inclination angle) is performed as a fine operation in a range up to a predetermined inclination angle of the electric joystick (e.g., −20 degrees to +20 degrees). Also, speed control (control to make the movement speed of the examination constant) is performed as a coarse operation in a range after exceeding the predetermined inclination angle of the electric joystick (e.g., −35 to −20 degrees, and +20 to +35 degrees).

Now, at the time of switching from coarse operations to fine operations, the electric joystick is in a tilted state. Accordingly, the range of inclination angle which can be used for fine operations in the direction in which the electric joystick is tilted is small, so it is difficult for the examiner to perform fine operations in the intended direction, and the operations may unintentionally switch to coarse operations. Accordingly, Japanese Patent Laid-Open No. 2009-56247 discloses the examiner returning the electric joystick to close to a neutral position (erect position) in order to facilitate smooth starting of fine operations after having performed coarse operations.

In a mechanism where a joystick and a stage unit are mechanically coupled, the examiner can perform coarse operations in a state where the joystick is in the neutral position, since a contact point between a supporting member in the shape of a hemisphere disposed at the lower portion of the joystick and a friction plate provided on the stage unit serves as an action fulcrum.

SUMMARY OF THE INVENTION

At least one ophthalmologic apparatus according to the present invention(s) includes: an examination unit configured to examine an eye to be examined; an operating member configured to be able to tilt in an optional direction; a first driving unit configured to drive the examination unit; a position control unit configured to control the first driving unit such that fine movement driving of the examination unit is performed in a case where a tilt angle of the operating member is smaller than a first angle, and coarse movement driving of the examination unit is performed in a case where the tilt angle of the operating member is equal to or greater than the first angle; a second driving unit configured to drive the operating member; and an angle control unit configured to control the second driving unit such that the tilt angle of the operating member is automatically changed to a second angle which is smaller than the first angle, in accordance with a change from the coarse movement to the fine movement.

At least one controlling method of an ophthalmologic apparatus according to the present invention(s) is a controlling method of an ophthalmologic apparatus including an examination unit configured to examine an eye to be examined and an operating member configured to be able to tilt in an optional direction. The method includes: controlling a first driving unit configured to drive the examination unit such that fine movement driving of the examination unit is performed in a case where a tilt angle of the operating member is smaller than a first angle, and coarse movement driving of the examination unit is performed in a case where the tilt angle of the operating member is equal to or greater than the first angle; and controlling a second driving unit configured to drive the operating member such that the tilt angle of the operating member is automatically changed to a second angle which is smaller than the first angle, in accordance with a change from the coarse movement to the fine movement. According to other aspects of the present invention(s), other apparatuses and methods are discussed herein.

Further features of the present invention(s) will become apparent from the following description of exemplary embodiments with reference to the attached drawings.

BRIEF DESCRIPTION OF THE DRAWINGS

FIGS. 4A through 4C are schematic diagrams illustrating detection actions by a first detecting unit.

FIGS. 5A through 5C are cross-sectional views of the operating unit with an operating rod tilted.

FIGS. 11A through 11C are explanatory diagrams of a separate configuration from a configuration where the operating unit according to the first embodiment is automatically returned to a non-inclined state.

DESCRIPTION OF THE EMBODIMENTS

Conventionally, there have been cases where, if the examiner is not accustomed to using an electric joystick, the operations of returning the electric joystick to around the neutral position before performing fine operations, after having performed coarse operations. It has been found desirable to improve the operability of the electric joystick.

According to an embodiment of the present invention, a tilting angle of an operating unit capable of being tilted in an optional direction can be automatically changed from to a second angle (e.g., 0 degrees) which is smaller than a first angle, in accordance with an examining unit changing from coarse movement to fine movement. Accordingly, fine movement after ending coarse method of the examination unit can be smoothly started by an examiner using an electric joystick. Thus operability of the electric joystick can be improved. Note that fine movement of the examination unit is performed if the tilt angle of the operating unit is smaller than the first angle, and coarse movement of the examination unit is performed if the tilt angle of the operating unit is equal to or greater than the first angle.

Now, this first angle is 20 degrees for example, but may be any other angle as long as an angle smaller than the limit of the tilt angle of the operating unit such that coarse movement of the examination unit can be performed. The second angle is 0 degrees for example, but may be any other angle as long as an angle smaller than the first angle and enabling the examiner to smoothly start fine movement. That is to say, an angle at which the examiner can start fine movement smoothly is conceivably 0 degrees, but is not restricted to this. A state where the tilt angle of the operating unit is at the second angle will be referred to in the present Specification as the operating unit being at a neutral position (erect position), or as the operating unit being in a non-tilted state.

Embodiments for carrying out the present invention will be described in detail with reference to the attached drawings.

First Embodiment

Figure 1:
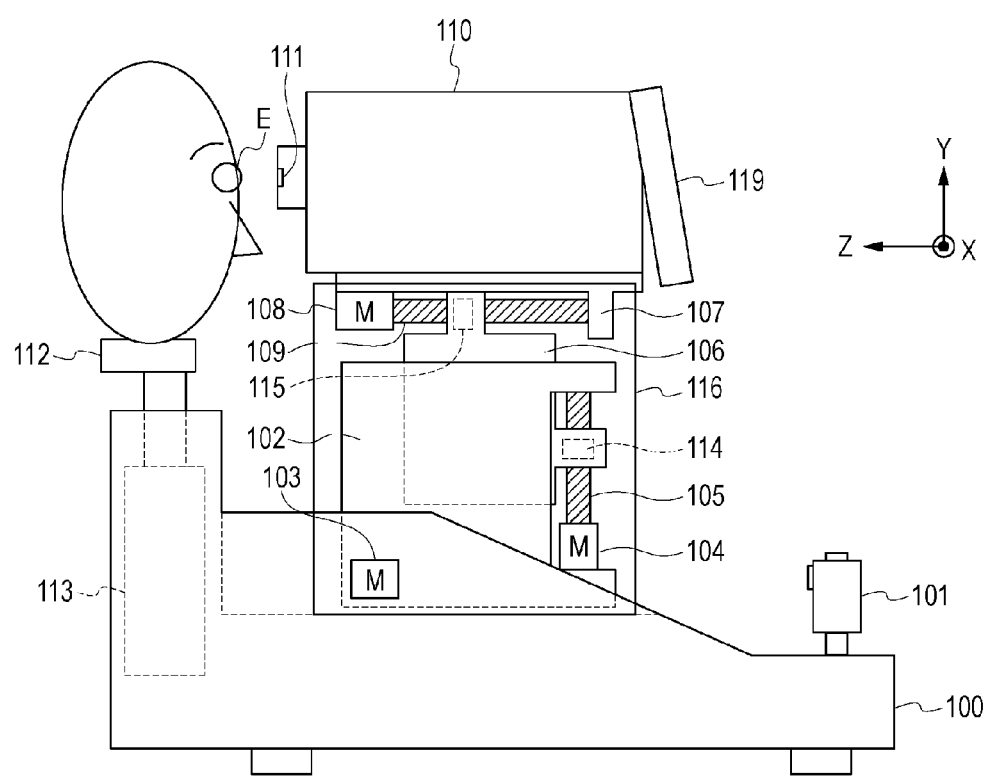
FIG. 1 is a diagram illustrating a schematic configuration of an ophthalmologic apparatus according to a first embodiment.

A first embodiment of the present invention will be described with reference to the drawings. FIG. 1 is a diagram illustrating a schematic configuration of an ophthalmologic apparatus according to the first embodiment. The ophthalmologic apparatus includes a base unit 100 which has a chinrest 112 for supporting the face of the subject, a driving unit 116 and operating unit 101 provided upon the base unit 100, and an examination unit 110 attached to the driving unit 116. The examination unit 110 has an optical system for performing examination, observation, photography, and so forth of the eye to be examined. A liquid crystal display (LCD) monitor 119, which is an example of a display unit for observation of the eye-to-be-examined E, is provided at the examiner side end of the examination unit 110. Note that the display unit does not necessarily have to be provided on the ophthalmologic apparatus. For example, the display unit may be a monitor connected to a computer in an ophthalmologic system having a computer connected to the ophthalmologic apparatus either by cable or wirelessly. The display unit may even be a rear surface monitor on a digital camera which is detachably mounted to the main unit of the ophthalmologic apparatus. The driving unit 116 is an example of a position changing unit which changes the position of the examination unit 110 as to the eye to be examined, and hereinafter may also be referred to as "driving unit" or "first driving unit".

The chinrest 112 is movable in a vertical direction (Y axis direction) by a driving mechanism 113. The examiner can instruct the driving direction, amount of driving, and driving speed of the driving unit 116, by tilting operations of the operating unit 101. Thus, the position of the examination unit 110, i.e., the position of the lens 111, can be aligned as to the eye-to-be-examined E, so examination, observation, photography, and so forth, can be performed. For example, in a case where the ophthalmologic apparatus is a non-mydriatic fundus camera, an illumination optical system having an observation light source whereby the eye to be examined is irradiated when performing observation, and an imaging light source for when performing photography, is provided. Also provided thereto is a photographic optical system for image formation of reflected light from the eye to be examined on an unshown imaging device, and so forth. In this example, reflected light from the eye to be examined that is cast from the illumination optical system is imaged on the imaging device via the photographic optical system, and a fundus image is displayed on the LCD monitor 119 and/or saved in unshown image memory as a still image. While the present embodiment is described by example of a non-mydriatic fundus camera, the ophthalmologic apparatus is not restricted to this arrangement, and application can be made to various types of ophthalmologic apparatuses, such as an optical coherence tomography (OCT) apparatus, an adaptive optics scanning laser ophthalmoscope (AO-SLO) apparatus, and so forth. The driving unit 116 moves the examination unit 110 in present X, Y, and Z directions, and accordingly has driving mechanisms corresponding to each of the axes.

X Axis

A frame 102 is movable in the horizontal direction (X axis direction) as to the base unit 100. The X-axis direction driving mechanism includes an X-axis driving motor 103 fixed on the base unit 100, an unshown feed screw coupled to an output shaft of the motor, and an unshown nut fixed to the frame 102 which is capable of moving the feed screw in the X axis direction. Rotation of the X-axis driving motor 103 causes the frame 102 to be driven in the X-axial direction by the feed screw and nut.

Y Axis

A frame 106 is movable in the vertical direction (Y axis direction) as to the frame 102. The Y-axis direction driving mechanism includes an Y-axis driving motor 104 fixed on the frame 102, a feed screw 105 coupled to an output shaft of the motor, and a nut 114 fixed to the frame 106 which is capable of moving the feed screw 105 in the Y axis direction. Rotation of the Y-axis driving motor 104 causes the frame 106 to be driven in the Y-axial direction by the feed screw 105 and nut 114.

Z Axis

A frame 107 is movable in the longitudinal direction (Z axis direction) as to the frame 106. The Z-axis direction driving mechanism includes a Z-axis driving motor 108 fixed on the frame 107, a feed screw 109 coupled to an output shaft of the motor, and a nut 115 fixed to the frame 107 which is capable of moving the feed screw 109 in the Z-axis direction. Rotation of the Z-axis driving motor 108 causes the frame 107 to be driven in the Z-axial direction by the feed screw 109 and nut 115.

Operating Unit 101

Figure 2:
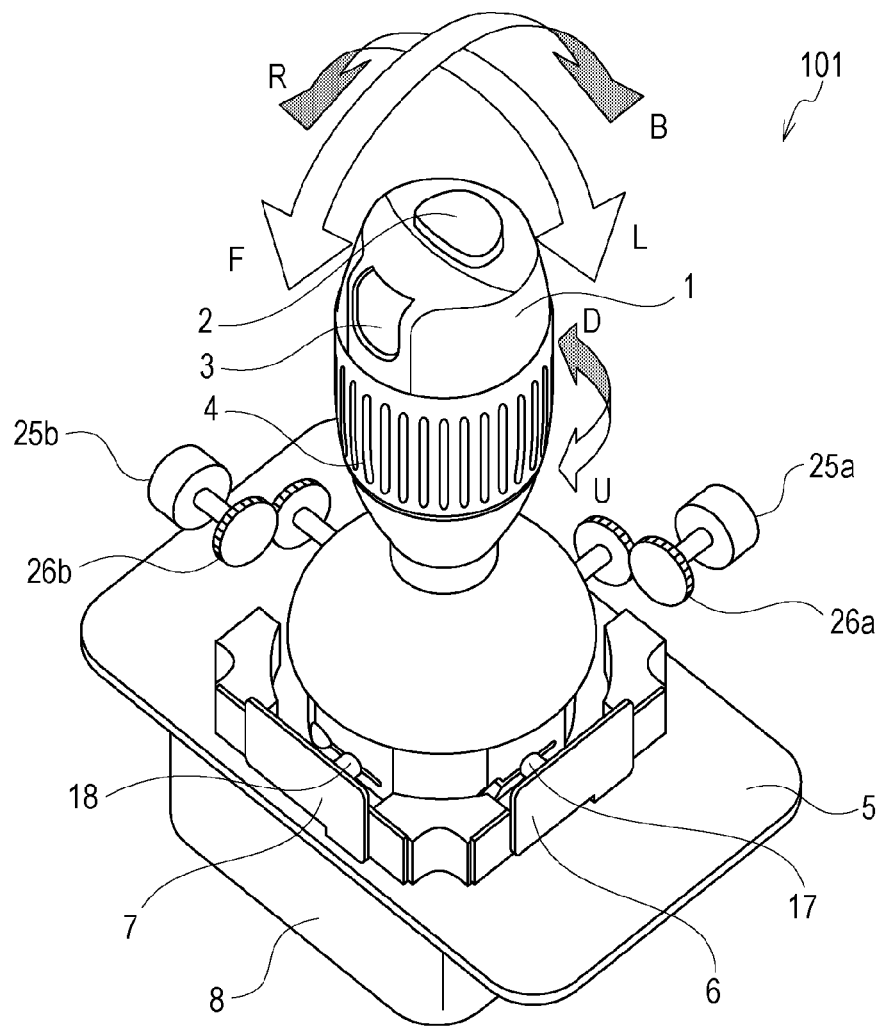
FIG. 2 is an external view of an operating unit according to the first embodiment.

FIG. 2 is a perspective view of the operating unit 101. The operating unit 101 is configured to move the examination unit 110 three-dimensionally, by instructing the driving direction, amount of driving, and driving speed of the driving unit 116. The operating unit 101 includes an operating rod 1, a measurement button 2, a function switch-over switch 3, a rotary dial 4, a bearing base 5, a first detecting unit 6, a second detecting unit 7, an operational force generating unit 8, a first slide pin 17, a second slide pin 18, operating rod driving units 25a and 25b, and operating rod driving couplers 26a and 26b.

In a case where the examiner has tilted the operating rod 1, which is a member for performing various types of operations, in the direction of the arrows L or R, the examination unit 110 moves in the interpupillary direction of the eye to be examined. In a case where the examiner has tilted the operating rod 1 in the direction of the arrows F or B, the examination unit 110 moves towards or away from the eye to be examined. When the examiner rotates the rotary dial 4, the examination unit 110 moves vertically. The measurement button 2 is disposed on the top of the operating rod 1. The measurement button 2 is used as a start button for examination, observation photography, and auto-alignment. Thus, the examiner can perform alignment through measurement by operating the operating unit 101. Other components will be described later.

Figure 3:
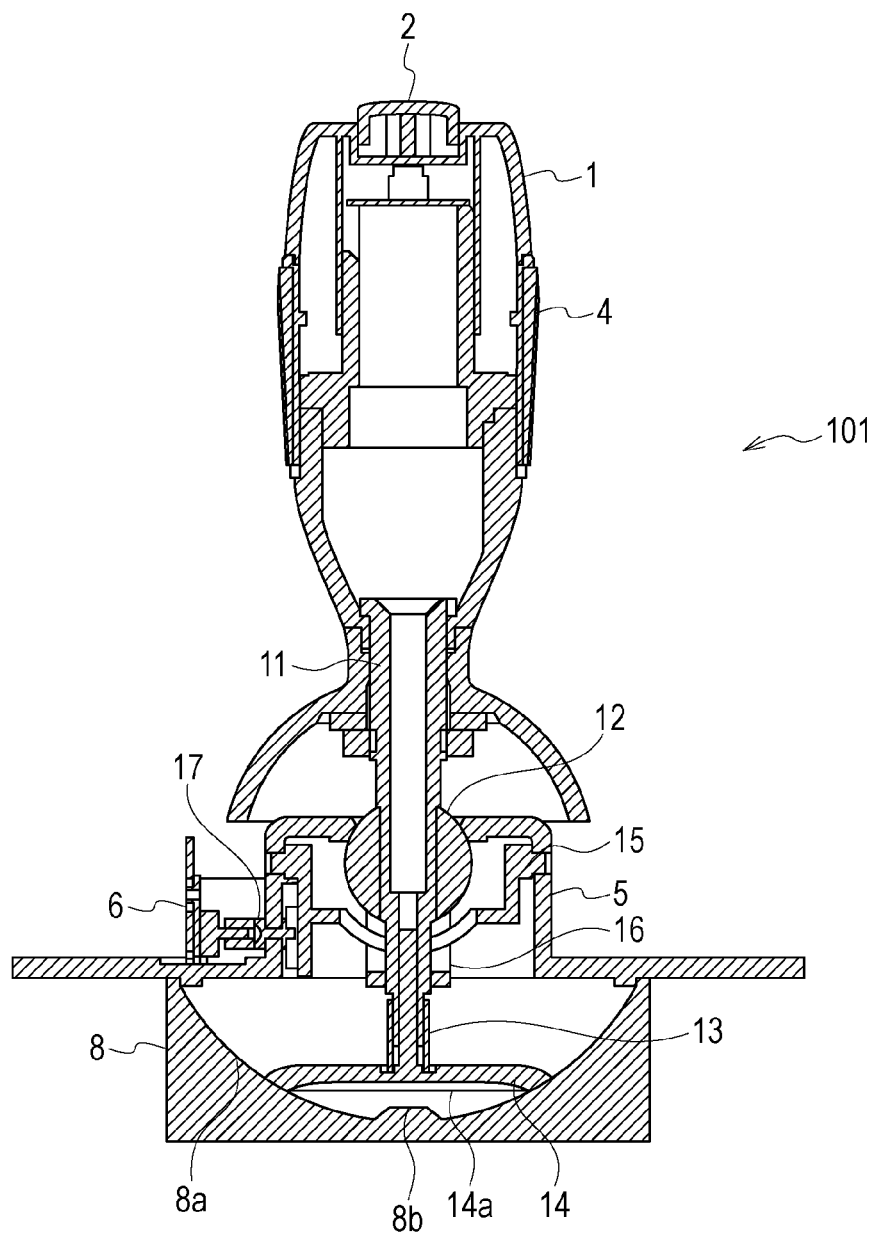
FIG. 3 is a cross-sectional view of the operating unit according to the first embodiment.

FIG. 3 is a cross-sectional view of the operating unit 101 illustrated in FIG. 2, taken along the L-R arrow direction. The operating unit 101 further includes an operating rod shaft 11, a center ball 12, a compression string 13, a movement unit 14, a first motion direction converting unit 15, and a second motion direction converting unit 16.

The operating rod shaft 11 is bonded within the operating rod 1. The bearing base 5 is disposed at the bottom of the operating unit 101, and the center ball 12 is attached to the operating rod shaft 11 below an opening portion of the bearing base 5. The center ball 12 has a spherical shape, and is urged to the opening portion of the bearing base 5 by the later-described compression string 13. Thus, tilting operations of the operating rod 1 can be performed centered on the curvature of the center ball 12 serving as the center member which is the fulcrum of the tilting operations.

Detection of Tilt Angle

Next, a mechanism whereby the operating unit 101 detects an inclination angle from a non-tilted position will be described. The first motion direction converting unit 15 and second motion direction converting unit 16, each having a recess shape, are disposed orthogonal to each other below the center ball 12 attached to the operating rod shaft 11. The first motion direction converting unit 15 and second motion direction converting unit 16 convert the tilting motion of the operating rod 1 into linear motion.

Rotation center shafts are formed on both ends of the first motion direction converting unit 15 and second motion direction converting unit 16, so as to fit a rotation center hole formed in the bearing base 5, and rotatably supported as to the rotation center hole of the bearing base 5. The rotation center hole is preferably the same height as the center of curvature of the center ball 12. A hole through which the operating rod shaft 11 passes is formed in the recessed portion of the first motion direction converting unit 15 and second motion direction converting unit 16, into which the operating rod shaft 11 is fit. Other components will be described later.

Now, the actions of the first motion direction converting unit 15 at the time of tilting the operating rod 1 in both directions of the arrows F-B will be described with reference to FIGS. 4A through 4C. A groove 15a is formed on one end of the first motion direction converting unit 15, in the same direction as the axial direction of the operating rod shaft 11, so that the first slide pin 17 fits therein. The first slide pin 17 is disposed fit into a groove 5a formed to the bearing base 5 as well, and is capable of moving in the horizontal direction in FIGS. 4A through 4C. The first slide pin 17 is bonded to an unshown input shaft of the first detecting unit 6. This first detecting unit 6 is a direct position detecting unit, and is a directly-operated potentiometer. Upon a tilting operation of the operating rod 1 being performed, the bonded operating rod shaft 11 also tilts as indicated in FIG. 4B, and accordingly, the first motion direction converting unit 15 into which the operating rod shaft 11 is fit rotates on rotation center shafts 15b on both ends. Upon the first motion direction converting unit 15 making a rotating action, the first slide pin 17 fit into the groove 15a moves along the groove 5a of the bearing base 5, and moves the input shaft of the first detecting unit 6. Due to the above-described action, the resistance value of the first detecting unit 6, which is the resistance value of the directly-operated potentiometer here, changes, and thus the tilt angle of the operating rod 1 can be detected.

The actions of detecting the tilt angle when tilting the operating rod 1 in both directions of the arrows L-R by the second motion direction converting unit 16, second slide pin 18, and second detecting unit 7, are performed in the same way as detection of the tilt angle in both directions of the arrows F-B as described above, so detailed description thereof will be omitted. Using the first detecting unit 6 and second detecting unit 7 as described above allows the tilt angle of the operating rod 1 as to an intended tilt direction to be uniquely detected.

While a direct position detecting unit has been described as being used in the present embodiment as the detecting unit, a detecting unit which detects rotational angle may be used. As one example of this arrangement, a method may be used where an input shaft of a rotary potentiometer may be bonded to one end of each rotation center shaft of the second motion direction converting unit 16. Alternatively, the detecting unit which detects rotational angle is not restricted to being a rotary potentiometer, and a method may be used where the tilt angle is detected using a sensor such as an encoder or the like.

Generating Urging Force by Compression String 13

Next, the configuration for generating operating force will be described. In FIG. 3, the movement unit 14 is disposed integrally with the operating rod 1 as a second member at the bottom of the operating rod shaft 11. A hollow part is formed at the lower end of the operating rod shaft 11. A center shaft of the movement unit 14 fits into the operating rod shaft 11, and the movement unit 14 can be slid as to the operating rod shaft 11 in the direction of the operating rod shaft 11. A disc-shaped portion where a recess 14a recessed at the middle portion is formed on the lower side of the center shaft of the movement unit 14. The operational force generating unit 8 (first member) is provided bonded to the bearing base 5 at the bottom of the movement unit 14. A generally spherical face 8a, centered on the center of curvature of the center ball 12, is formed on the operational force generating unit 8. A protrusion 8b having a protruding shape is formed at the middle portion of the generally spherical face 8a, thus forming a returning member. The compression string 13, which is an elastic body, is provided between the operating rod shaft 11 and the movement unit 14. The compression string 13 generates urging force by being compressed, so as to press the center ball 12 against the bearing base 5 as described above by this urging force, and also to press the movement unit 14 against the operational force generating unit 8.

Actions of Operating Unit 101

Now, the actions of the operating unit 101 in a case where the operating rod 1 has been operated so as to tilt will be described with reference to FIGS. 5A through 5C. FIGS. 5A through 5C are cross-sectional views of the operating unit 101 illustrated in FIG. 2, taken along the L-R arrow direction.

FIG. 5A illustrates the neutral state of the operating rod 1. FIG. 5B illustrates a state where the operating rod 1 has been tilted to a predetermined angle $\theta_1$. FIG. 5C illustrates a state where the operating rod 1 has been tilted to a predetermined angle $\theta_2$. The predetermined angle $\theta_1$ is the maximum tilt angle in a tilt retaining region, and the predetermined angle $\theta_2$ is the maximum tilt angle in a tilt returning region.

First, A case where the operating rod 1 is tilted within the tilt retaining region (from tilt angle $\theta_0$ to $\theta_1$). In the tilt retaining region, the movement unit 14 is pressed against the generally spherical face 8a of the operational force generating unit 8 by the compression string 13. At this time, friction force is generated between the movement unit 14 and the operational force generating unit 8, and the tilt angle of the operating rod 1 can be retained by this friction force. Also, The generally spherical face 8a of the operational force generating unit 8 is formed having a curvature where the center of tilt is the center, so the compression string 13 does not stretch or compress within the tilt regaining region even if moved in an optional direction. Accordingly, constant friction force can be generated regardless of the direction of operation of the operating rod 1, and accordingly the operating force can be maintained constant in the optional direction.

Next, a case where the operating rod 1 is tilted to the tilt returning region will be described. Upon the examiner tilting the operating rod 1 to the tilt returning region, an inclined face formed on the periphery of the recess 14a of the movement unit 14 comes into contact with a return portion (protrusion) 8b of the operational force generating unit 8 (see FIG. 5B). Upon the examiner further tilting the operating rod 1, the movement unit 14 moves in the axial direction (the direction to the obliquely upper right in FIG. 5B) due to the component of the force in the axial direction of the operating rod shaft 11, received from the inclined face, as illustrated in FIG. 5C. The compression string 13 is compressed at this time. Here, extra operating force is necessary to deal with the compressed compression string 13, equivalent to the amount of force of the compression string 13 having been compressed, so the examiner can recognize that operation has reached the tilt returning region. If the examiner stops gripping the operating rod 1, force to return to the center direction is generated at the movement unit 14 due to the force of the compression string 13 trying to extend. The operating rod shaft 11 and the operating rod 1 return to the predetermined angle $\theta_1$ illustrated in FIG. 5B, due to this returning force.

Functional Block Diagram

Figure 6:
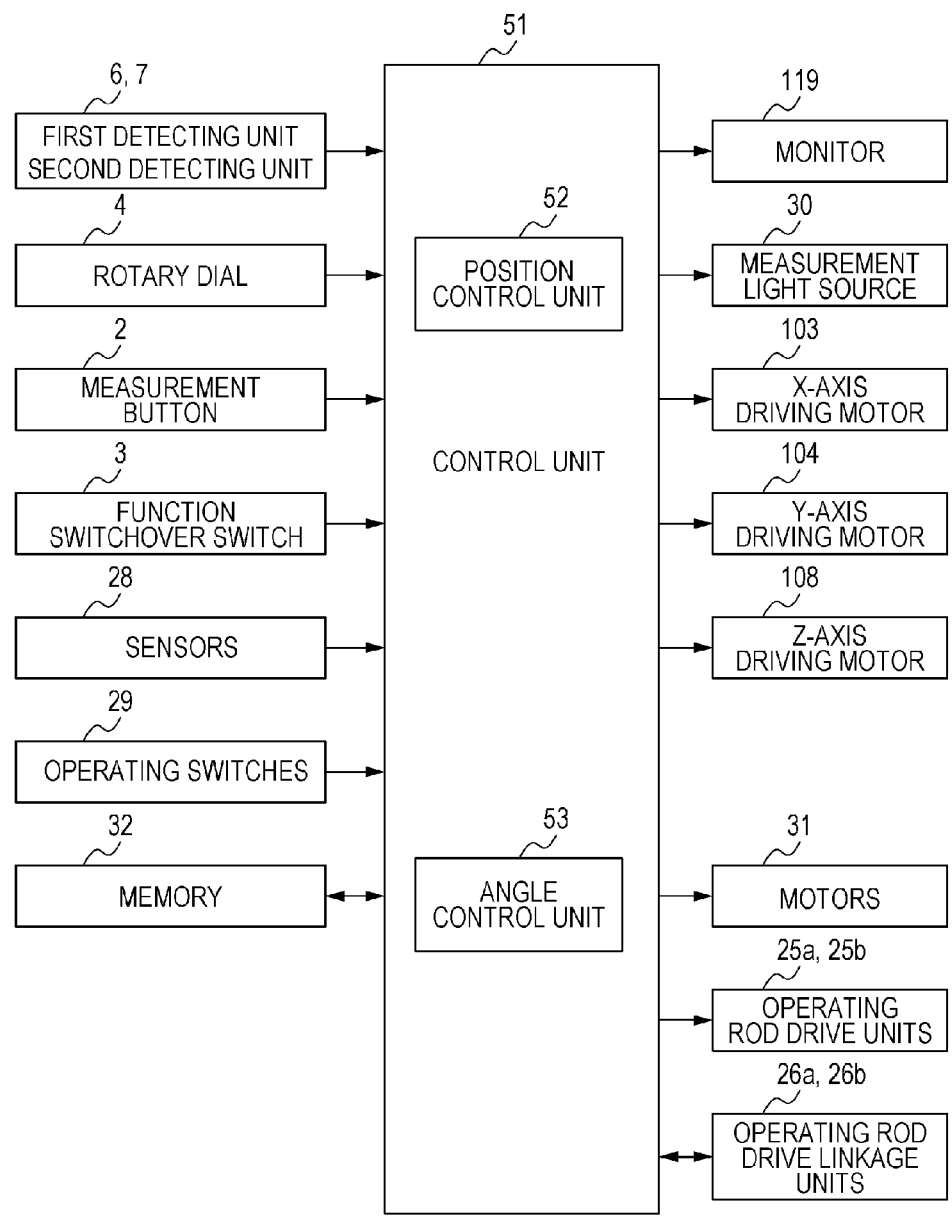
FIG. 6 is a functional block diagram according to the first embodiment.

Next, FIG. 6 is a functional block diagram for describing control according to the present embodiment. The ophthalmologic apparatus according to the present embodiment functions as an ophthalmologic apparatus to examine an eye to be examined, by being controlled by a control unit 51. First, the first detecting unit 6 and second detecting unit 7 at the operating unit 101 are connected to the control unit 51 via an unshown A/D converter. The control unit 51 is also connected to the X-axis driving motor 103 and the Z-axis driving motor 108. A position control unit 52 in the control unit 51 controls the X-axis driving motor 103 and the Z-axis driving motor 108 by transmitting driving signals thereto, based on signals from the first detecting unit 6 and second detecting unit 7 input from the A/D converter. A rotary dial on the operating unit 101 is connected to the control unit 51. The control unit 51 is also connected to sensors 28 and operating switches 29, the outputs of which are input to the control unit 51. The monitor 119, a measurement light source 30, motors 31, the operating rod driving units 25a and 25b, the operating rod driving couplers 26a and 26b, and memory 32 are further connected to the control unit 51. An angle control unit 53 of the control unit 51 transmits driving signals to the operating rod driving units 25a and 25b so as to control them, for example. Note that the control unit 51 performs control which includes detection of these various types of input signals, analysis of the input signals, and various types of output. The sensors 28 are limit sensors for detecting the movement limit of driving units, and so forth. The operating switches 29 are switches for the examiner to perform various types of settings. The measurement light source 30 is a light source to illuminate the eye-to-be-examined E, to observe and photograph the eye-to-be-examined E. The motors 31 are motors used to adjust the height of the chinrest 112, and to drive the optical system configured within the examination unit 110. The memory 32 is memory which enables writing and readout of various types of data.

Figure 7A:
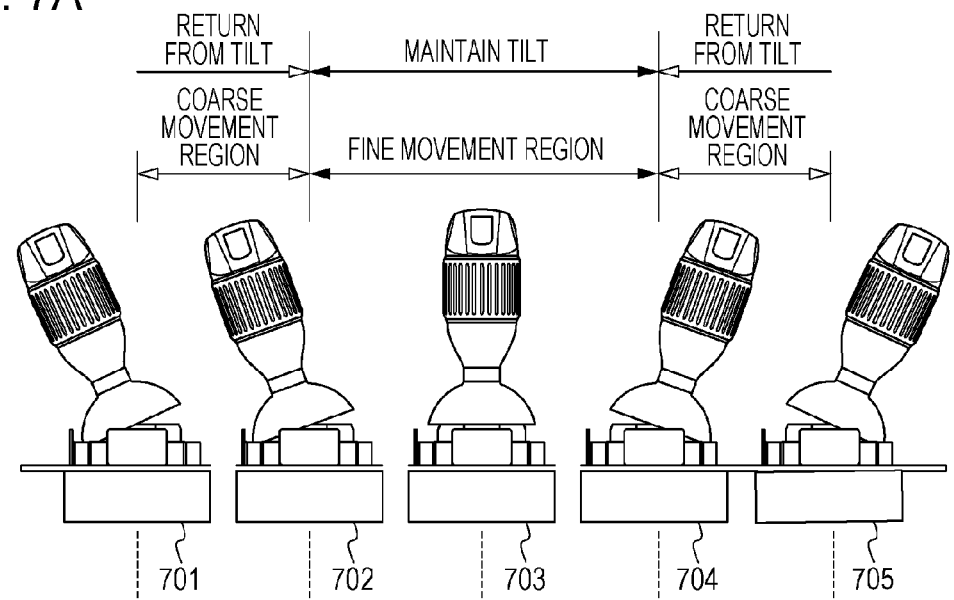
FIGS. 7A through 7C are schematic diagrams illustrating tilted attitude of the operating rod, output of the detecting unit, and movement of the examination unit.
Figure 7B:
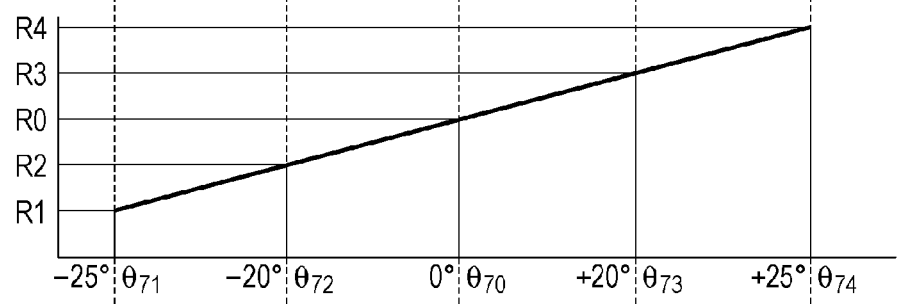
Figure 7C:
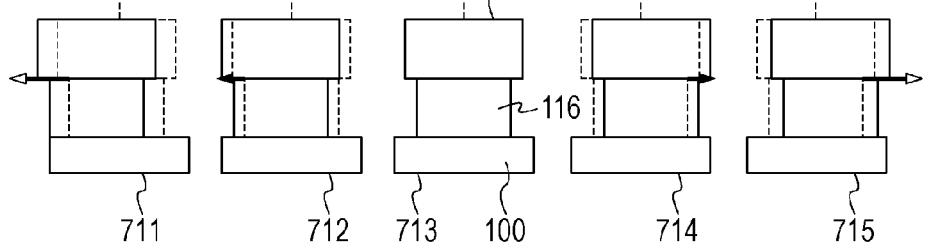

Relationship Between Tilt Angle of Operating Unit, Resistance Value of Detecting Unit, and Movement of Examination Unit FIG. 7A is a diagram illustrating an attitude 701 through an attitude 705 of the operating unit 101 as to the tilt angle θ of the operating rod 1 along the L-R arrow direction. FIG. 7B is a diagram illustrating the relationship between attitude 701 through attitude 705 of the operating unit 101 and a resistance value R which is the output of the second detecting unit 7. FIG. 7C is a diagram illustrating an operating status 711 through operating status 715 of the examination unit 110 at attitude 701 through attitude 705 of the operating unit 101. The respective tilt angles are −25° for $\theta_{71}$, −20° for $\theta_{72}$, 0° for $\theta_{70}$, +20° for $\theta_{73}$, and +25° for $\theta_{74}$. The resistance values R1, R2, R0, R3, and R4 correspond to the tilt angles $\theta_{71}$, $\theta_{72}$, $\theta_{70}$, $\theta_{73}$, and $\theta_{74}$, respectively.

In a case where the operating rod 1 is in a region of −20° through +20°, corresponding to the resistance values R2, R0, and R3, the tilt angle of the operating rod 1 is retained by the above-described mechanism. At this time, the control unit 51 controls the driving position of the X-axis driving motor 103 based on the output of the second detecting unit 7 which changes according to the tilt angle of the operating rod 1. This enables fine alignment.

Also, in a case where the operating rod 1 is in a region of −25° through −20°, corresponding to the resistance values R1 and R2, or a region of +20° through +25°, corresponding to the resistance values R3 and R4, the tilt angle of the operating rod 1 returns to the predetermined angle $\theta_{72}$ or the predetermined angle $\theta_{73}$ by the above-described mechanism. At this time, the control unit 51 controls the driving speed of the X-axis driving motor 103 based on the output of the second detecting unit 7 which changes according to the tilt angle of the operating rod 1. This enables major movement of the examination unit 110.

Figure 8A:
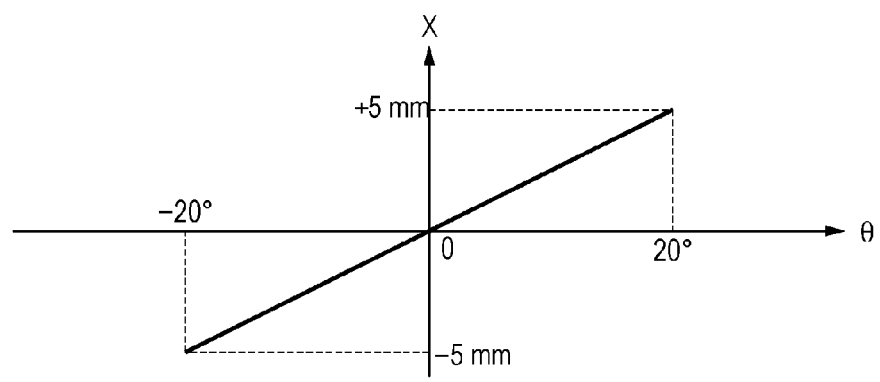
FIGS. 8A and 8B are diagrams for describing control in a fine movement region and coarse movement regions.

FIG. 8A illustrates movement amount X of the operating unit 101 in the L-R directions, as to the tilt angle θ of the operating rod 1 in the L-R directions. The tilt angle $\theta_0$ of the operating rod 1 when erect is 0°.

Figure 8B:
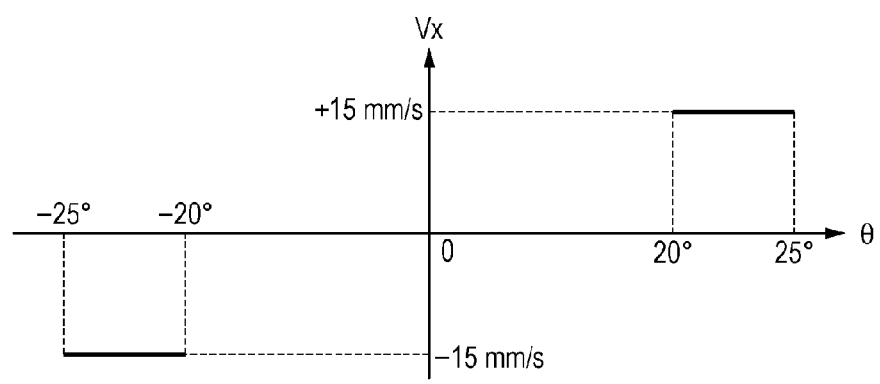

In a case where the examiner has maintained the tilt angle θ of the operating rod 1 in a range of −20° to +20°, the control unit 51 controls the X-axis driving motor 103 such that the examination unit 110 moves within a range of −5 mm to +5 mm, in proportion to the tilt angle θ from 0°. FIG. 8B illustrates the moving speed Vx of the operating unit 101 in the L-R direction, as to the tilt angle θ of the operating rod 1 in the L-R directions. In a case where the examiner maintains the tilt angle θ in a range which exceeds −20° but does not reach −25°, the control unit 51 controls the X-axis driving motor 103 so as to move the examination unit 110 in the direction of tilt of the operating rod 1, at a speed of 15 mm/second. Similarly, in a case where the examiner maintains the tilt angle θ in a range which exceeds +20° but does not reach +25°, the control unit 51 controls the X-axis driving motor 103 so as to move the examination unit 110 in the direction of tilt of the operating rod 1, at a speed of 15 mm/second. Description has thus been made regarding the control method of the control unit 51 in a case where the examiner has tilted the operating rod 1 in the L-R (left and right) directions, but the same control is performed in a case of the operating rod 1 being tilted in the F-B (front and back) directions, so detailed description thereof will be omitted.

Relationship Between Anterior Eye Portion Image and Alignment State

Figure 9A:
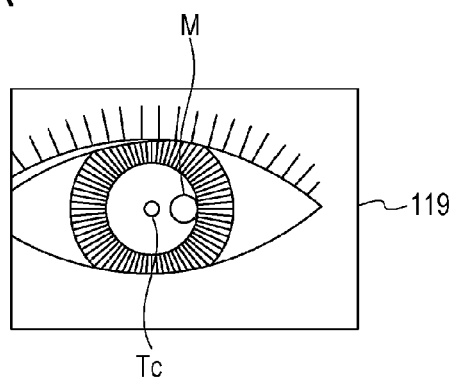
FIGS. 9A and 9B are explanatory diagrams of a proximity state and a separated state of the center of an eye to be examined and an alignment mark on a monitor.

FIG. 9A is an explanatory diagram of an anterior eye portion image of the eye-to-be-examined E on the LCD monitor 119. The LCD monitor 119 displays a state where an eye-tobe-examined center Tc and an alignment mark M are only slightly apart. When aligning the examination unit 110 in the horizontal direction, the examiner operates the operating rod 1 so that the eye-to-be-examined center Tc comes into the alignment mark M. In this case, the eye-to-be-examined center Tc and the alignment mark M are only slightly apart, so the examiner attempts fine alignment. If a configuration is employed where the eye-to-be-examined center Tc is moved by an amount proportionate to the tilt angle θ of the operating rod 1, and the eye-to-be-examined center Tc is moved too far, this can be handled by returning the tilt angle θ of the operating rod 1 so as to return the distance moved too far, so operability improves for the examiner.

Figure 9B:
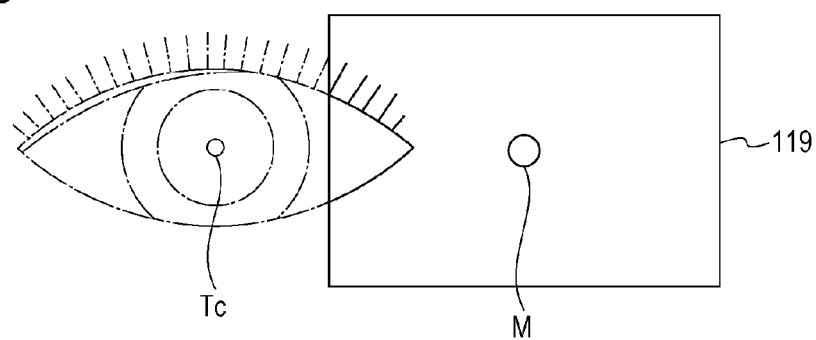

FIG. 9B is an explanatory diagram of the eye-to-be-examined E on the LCD monitor 119. This illustrates a case where the eye-to-be-examined center Tc and the alignment mark M are far apart, unlike the case in FIG. 9A. In this case, the examiner wants to move the eye-to-be-examined center Tc to nearby the alignment mark M speedily, and accordingly continues to tilt the operating rod 1 past a tilt angle θ of 20° against the returning force thereof, as described above. Accordingly, the examination unit 110 moves in the direction of tilt of the operating rod 1 at a constant speed of 15 mm/second, which enables speedy positioning. The examiner then reduces the force applied to the operating rod 1, once the eye-to-be-examined center Tc has come close to the alignment mark M as illustrated in FIG. 9A. Accordingly, the operating rod 1 returns to the position where the tilt angle θ is 20° by the returning force, and once the tilt angle is within the predetermined tilt angle (20° or less), the speed control switches to position control (distance control), so fine alignment can be performed thereafter.

Alignment of the examination unit 110 in the F-B (front and back) directions is performed in the same way as with alignment of the examination unit 110 in the L-R (left and right) directions. In a case where the examination unit 110 is near the best focus position and fine focus adjustment is to be performed, the examiner tilts the operating rod 1 to the range within the −20° to +20° where the friction force acts, and performs position control. In a case where the focus is not close to the best focus position, the examiner tilts the operating rod 1 against the returning force beyond 20° to perform speed control.

In a case where alignment is off in both F-B (front and back) directions and L-R (left and right) directions, The examiner can perform alignment of both at the same time by tilting the operating rod 1 in a diagonal direction. According to the present embodiment, an operating unit 101 with constant operating force regardless of the operating direction can be realized, thus enabling faster and finer alignment.

Configuration of Automatically Moving Operating Unit to Neutral Position

Now, the operating rod driving units 25a and 25b which are an example of driving members in the operating unit 101 are driving motors, for example. The operating rod driving units 25a and 25b are coupled to the operating rod 1 via the operating rod driving couplers 26a and 26b which are an example of couplers in the operating unit 101. The operating rod driving couplers 26a and 26b preferably have gears provided on the opposite side of the first slide pin 17 and second slide pin 18, which are an example of moving members, from the operating rod 1. Accordingly, the power from the operating rod driving units 25a and 25b can be transmitted to the first slide pin 17 and second slide pin 18 via the operating rod driving couplers 26a and 26b. Thus, the first slide pin 17 and second slide pin 18 can be moved such as illustrated in FIGS. 4A through 4C, based on control signals from the control unit 51, whereby the tilt angle of the operating rod 1 can be automatically changed. According to the present embodiment, the operating rod driving units 25a and 25b are controlled based on control signals from the angle control unit 53 in the control unit 51 after a coarse operation has ended, and before starting a fine operation, such that the state of the operating rod 1 is automatically changed to a non-tilted state (moved to the neutral position). Accordingly, examiners who are not accustomed to using electric joysticks can also smoothly start fine operations after ending coarse operations. Thus, operability of the electric joystick can be improved.

When the state of the operating rod 1 is being automatically changed to a non-tilted state after coarse operations have been finished, an unshown display control unit in the control unit 51 preferably displays a message to this effect on the LCD monitor 119. Accordingly, the examiner can know that if the state of the operating rod 1 starts being automatically changed to a non-tilted state while operating the electric joystick, he/she should wait till the changing of the state of the operating rod 1 to the non-tilted state ends before starting fine operations.

Now, the operating rod driving couplers 26a and 26b preferably have a switching mechanism to switch transmission of the power from the operating rod driving units 25a and 25b on and off. The switching mechanism is preferably an electromagnet capable of switching between on and off depending on whether electrified or not (e.g., a clutch mechanism). The switching mechanism can switch between a state where power from the operating rod driving units 25a and 25b is transmitted to the operating rod 1 and a state where the power is not transmitted thereto. Accordingly, in a case where the examiner is operating the operating rod 1, the switching mechanism can switch to a state where the power from the operating rod driving units 25a and 25b is not transmitted to the operating rod 1. Thus, the examiner can tilt the operating rod 1 without feeling a load due to the operating rod driving units 25a and 25b. The timing of the switching mechanism switching to the state where the power from the operating rod driving units 25a and 25b is transmitted to the operating rod 1 is preferably after coarse operations have ended and before automatically returning the operating rod 1 to the neutral position, which will be described later. The state in which power from the operating rod driving units 25a and 25b is not transmitted to the operating rod 1 due to the switching mechanism of the operating rod driving couplers 26a and 26b is the initial state.

Such an angle changing unit, which is the configuration that moves the operating rod 1 to the neutral position, is not restricted to the operating rod driving units 25a and 25b and operating rod driving couplers 26a and 26b such as described above. This angle changing unit will also be referred to as a "second driving unit". Another configuration for automatically returning the operating unit according to the present embodiment to a non-tilted state will be described with reference to FIGS. 11A through 11C. FIG. 11A illustrates the initial state in which the operating rod 1 is in the non-tilted state, which is the same state as illustrated in FIG. 5A, but the configuration of the operational force generating unit 8 is partly different. Specifically, elastic members 38a and 38b are provided as an angle changing unit between the operational force generating unit 8 and the bearing base 5. The operating rod 1 is tilted as illustrated in FIG. 11B, which is the same action as in FIG. 5B. Stoppers or the like are preferably provided between the bearing base 5 and the operational force generating unit 8 so that force is not applied to the elastic members 38a and 38b at this time. At the time of the operating rod 1 automatically moving to the neutral position, the operational force generating unit 8 is moved upwards by a distance 40, by a mechanism 39 provided below the operational force generating unit 8 as illustrated in FIG. 11C, which compresses the compression string 13. Thus, the operating rod 1 can be changed to the non-tilted state which is a stable state. Accordingly, the operating rod 1 can be automatically moved to the neutral position, by the operational force generating unit 8 being pressed upwards by the mechanism 39 provided at the bottom thereof, based on control signals from the angle control unit 53 of the control unit 51.

Timing of Automatically Moving Operating Unit to Neutral Position

Next, a control method of the examination unit 110 when the examiner operates the electric joystick will be described. The electric joystick according to the present embodiment switches between fine operations and coarse operations based on the tilt angle θ detected by the first detecting unit 6 and the second detecting unit 7. In a case where the tilt angle θ of the operating rod 1 is smaller than the predetermined angle $θ_1$, driving control of the driving unit 116 is performed so that the tilt angle of the operating rod 1 and the position of the examination unit 110 correlated, thus functioning as fine operations. On the other hand, in a case where the tilt angle θ of the operating rod 1 is the predetermined angle $θ_1$ or greater, driving control of the driving unit 116 is performed so that the tilt angle of the operating rod 1 and the moving speed of the examination unit 110 correlated, thus functioning as coarse operations. Thus, with the electric joystick where the driving mode of the examination unit 110 is switched according to the tilt angle θ of the operating rod 1, the alignment state between the examination unit 110 and the eye-to-be-examined E can be determined by detecting the tilt angle θ of the operating rod 1. For example, in a case where the tilt angle θ of the operating rod 1 is operated from the predetermined angle $θ_1$ or greater (coarse operations) to below the predetermined angle $θ_1$ (fine operations), determination can be made that coarse alignment has been completed. Alternatively, an arrangement may be made where, in a case where the tilt angle θ of the operating rod 1 is operated from the predetermined angle $θ_1$ or greater (coarse operations) to below the predetermined angle $θ_1$ (fine operations), and there is no change for a predetermined amount of time, determination is made that coarse alignment has been completed.

That is to say, the first detecting unit 6 and second detecting unit 7 can be used as detecting units to detect that coarse alignment, which is coarse movement, has been completed, and changed to fine alignment, which is fine movement. In the present embodiment, description is made regarding a technique where the tilt angle θ detected by the first detecting unit 6 and second detecting unit 7 is used to detect changing from coarse movement to fine movement, but a later-described function switch-over switch 3 or the like may be used as a detection unit.

Flowchart

Figure 10:
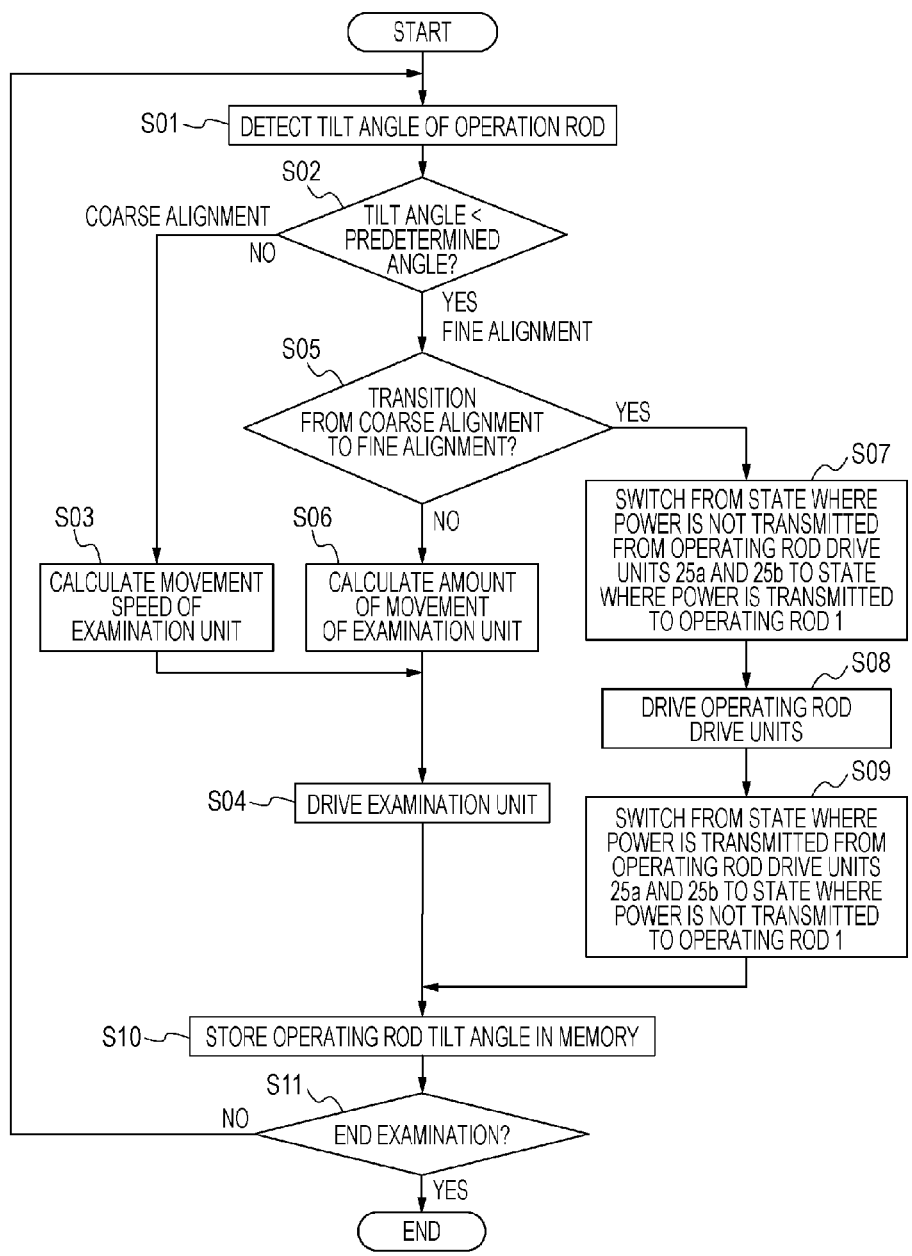
FIG. 10 is a flowchart for describing control of the examining unit and the operating rod according to the first embodiment.

FIG. 10 is a flowchart illustrating control which the control unit 51 executes, regarding a tilting operation being performed at the operating rod 1 and the examination unit 110 being driven. Note that control of the stage in the X-axis direction in a case of having tilted the operating rod 1 in the L-R arrow directions, and control of the stage in the Z-axis direction in a case of having tilted the operating rod 1 in the F-B arrow directions, can be performed by the same method. Accordingly, description will be made regarding the X axis, to simplify description.

First, in step S01, upon the examiner tilting the operating rod 1 in the X-axis direction to align the eye-to-be-examined E and the examination unit 110, the output value of the first detecting unit 6 is transmitted to the control unit 51, and the tilt angle θ of the operating rod 1 is detected. Next, in step S02, the detected tilt angle θ is compared with the predetermined angle, and the magnitude is determined. In a case where determination is made in step S02 that the tilt angle has exceeded the predetermined angle, meaning that the operating rod 1 has been tilted far in the X-axis direction, the flow advances to step S03. In step S03, the movement speed of the examination unit 110 is decided based on the tilt angle of the operating rod 1. The flow then proceeds to step S04, where the control unit 51 controls the X-axis driving motor 103 such that the examination unit 110 moves at the speed which has been decided. Note however, that there is an upper limit to the rotational speed of the driving motor moving the examination unit 110, and moving too fast is undesirable from safety reasons as well, so an upper limit is provided for the moving speed. This control allows the speed at which the examination unit 110 moves to be adjusted even in a case where the operating rod 1 is tilted greatly for coarse movement of the examination unit 110.

On the other hand, in a case where the tilt angle θ is determined to be within the predetermined angle in step S02, the flow advances to step S05. In step S05, the control unit 51 references the tilt angle θ of the operating rod 1 stored in the memory 32, and determines whether the alignment operation has switched from coarse alignment to fine alignment, or whether fine alignment is being continued. In a case where fine alignment is being continued, the flow advances to step S06, and an amount of movement of the operating unit 101 corresponding to the tilt angle θ of the operating rod 1 detected by the first detecting unit 6 is calculated. The flow then proceeds to step S04, where the control unit 51 controls rotation of the X-axis driving motor 103 such that the examination unit 110 moves the calculated amount. The control unit 51 can control the position of the examination unit 110 according to the tilt angle of the operating rod 1 by repeating the above steps, and thus can perform fine movement of the examination unit 110 so as to be accurately aligned with the eye to be examined.

On the other hand, in a case where determination is made in step S05 that the alignment operation has been switched from coarse alignment to fine alignment, the control unit 51 controls the operating rod driving unit 25a and the operating rod driving coupler 26a so as to return the operating rod 1 to the neutral position. First, in step S07, the control unit 51 controls the operating rod driving coupler 26a so as to link the operating rod 1 to the operating rod driving unit 25a. That is to say, the control unit 51 switches the state where power is not transmitted from the operating rod driving unit 25a to the operating rod 1, to a state where power is transmitted. In step S08, the control unit 51 drives the operating rod driving unit 25a so as to automatically return the operating rod 1 to the neutral position. After the operating rod 1 having been automatically returned to the neutral position, in step S09 the control unit 51 controls the operating rod driving coupler 26a so as to cut off connection with the operating rod driving unit 25a, so that there is no load felt at the hand of the examiner thereafter. That is to say, the control unit 51 switches the state from where power is transmitted from the operating rod driving unit 25a to the operating rod 1, to a state where power is not transmitted.

The tilt angle of the operating rod 1 detected by the first detecting unit 6 is stored in the memory 32 in step S10. The stored tilt angle is used to determine change in operations of the operating rod 1. In step S11, determination is made regarding whether or not to end the examination. The above steps are repeated until the examination ends, whereby the control can be made to return the operating rod 1 to the neutral position when the coarse alignment ends.

Thus, by returning the operating rod 1 to the neutral position at the time of ending coarse alignment, subsequent fine operation can always be started from a state where the operating rod 1 is at the neutral position. Accordingly, the examiner performing fine movement can efficiently perform alignment operations in the direction in which coarse operations had been performed, in the same way as in the opposite direction, thereby improving operability of the electric joystick.

Function Switch-Over Switch 3

Next, the function switch-over switch 3 will be described. The function switch-over switch 3 is an example of a switch to transmit a signal to the angle control unit 53 in the control unit 51. A signal indicating change from coarse movement to fine movement of the examination unit 110 can be transmitted to the control unit 51 by the examiner pressing the function switch-over switch 3. Accordingly, the operating unit 101 can be automatically changed to the neutral position by the angle control unit 53 of the control unit 51.

Also, the function switch-over switch 3 may be used for switching between multiple modes of the ophthalmologic apparatus (e.g., multiple observation modes or multiple operation modes). For example, in a case where the ophthalmologic apparatus is a fundus camera, switching can be performed from a state where the anterior eye portion of the eye to be examined is being observed, to a state where the fundus is being observed. Also, the function switch-over switch 3 can function as an operation invalidation unit. For example, the control unit 51 transmits driving signals to the X-axis driving motor 103 and Z-axis driving motor 108 based on signals from the first detecting unit 6 and second detecting unit 7 input via the unshown A/D converter, and signals from the operation invalidation unit. At this time, the operation invalidation unit is a momentary button, and invalidation signals forbidding driving are transmitted to the control unit 51 as long as the examiner is pressing the function switch-over switch 3. Accordingly, operability of fine alignment by fine motion operations can be improved, by the examiner operating the operation invalidation unit at the point that the alignment is in a generally completed state as illustrated in FIG. 9A, so as to return the operating rod 1 to the neutral state while operating the operation invalidation unit. Also, while description has been made in the present embodiment that fine motion and speed control is performed for the operating rod 1 being tilted in the F-B (front and back) directions in the same way as with the L-R (left and right) directions, but the present invention is not restricted thusly. For example, an arrangement may be made where, if the operating rod 1 is tilted to the coarse movement region in the F (front) direction, the control unit 51 forbids transmission of the driving signals to the Z-axis driving motor 108. This prevents coarse movement operations due to operation error by the examiner during alignment operations, and thus can prevent contact between the eye-to-be-examined E and the examination unit 110. This also does away with the possibility that the examination unit 110 will approach the eye-to-be-examined E in close proximity at high speed, so subject anxiety can be reduced.

Second Embodiment

Operating Unit Automatically Returns to Neutral Position after Completion of Automatic Alignment A second embodiment will be described. In the present embodiment, the ophthalmologic apparatus has an automatic alignment function. This automatic alignment where alignment of the eye-to-be-examined E and the examination unit 110 is performed automatically without the examiner operating the operating rod 1, and manual alignment where the examiner manually operates the operating rod 1, can be switched between. For example, alignment equivalent to coarse operation of the operating rod 1 may be performed automatically, and after the automatic alignment being completed, alignment is switched to manual alignment which is equivalent to fine operation of the operating rod 1. At this time, the operating rod 1 automatically tilts in accordance with movement of the examination unit 110 during automatic alignment if electrical connection has not been cut off. Accordingly, the electric joystick is automatically returned to the neutral position after the automatic alignment is completed.

The ophthalmologic apparatus according to the present embodiment has a camera sensor (omitted from illustration) for comprehending the position of the eye-to-be-examined E as to the examination unit 110, so as to perform automatic alignment, in addition to the configurations described in the first embodiment. The camera sensor which is an example of an image acquiring unit acquires images of the anterior eye portion of the eye to be examined, and outputs the acquired images to the control unit 51. An unshown calculating unit in the control unit 51 calculates the positional shift amount between the eye-to-be-examined E and the examination unit 110, from the output image of the camera sensor. The examination unit 110 is driven in relation to the base unit 100 by driving the X-axis driving motor 103, Y-axis driving motor 104, and Z-axis driving motor 108, based on the calculated positional shift amount, thereby realizing automatic alignment. An unshown determining unit in the control unit 51 can determine the alignment state by comparing the calculated positional shift amount with a threshold value. For example, determination can be made that automatic alignment serving as coarse alignment is being performed if the calculated positional shift amount is equal to or greater than the threshold value, and that fine alignment should be performed if the calculated positional shift amount is smaller than the threshold value. Depending on the result of the determination, the movement of the examination unit 110 is stopped, and control to automatically return the operating rod 1 described in the first embodiment is performed. The camera sensor is used at this time as a detecting unit to detect that movement has been switched form coarse movement to fine movement. While a case of automatically detecting completion of automatic alignment has been described, the present invention is not restricted thusly. For example, an alignment switchover switch (not illustrated) is preferably provided in the ophthalmologic apparatus according to the present embodiment, to switch between automatic alignment and manual alignment. In a case where automatic alignment is being performed, and the examiner presses the alignment switchover switch, the control unit 51 stops movement of the examination unit 110 and switches to manual alignment. Thereafter, in a case where a detecting unit detects that coarse alignment, which is coarse movement, has been completed, the control unit 51 controls the operating rod driving units 25a and 25b and operating rod driving couplers 26a and 26b to return to the operating rod 1 to the neutral position, in the same way as with the first embodiment.

Accordingly, in a case where the examiner desires to perform manual fine adjustment of the alignment state when examining an eye to be examined, the joystick can be operated from a state where the operating rod 1 is in the neutral position, thereby improving operability.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention(s) have been described with reference to exemplary embodiments, it is to be understood that the invention(s) are not limited to the disclosed exemplary embodiments. The scope of the following claims is to be accorded the broadest interpretation so as to encompass all such modifications and equivalent structures and functions.

This application claims the benefit of Japanese Patent Application No. 2013-262760, filed Dec. 19, 2013, which is hereby incorporated by reference herein in its entirety.

What is claimed is:

1. An ophthalmologic apparatus comprising:
    an examination unit configured to examine an eye to be examined;
    an operating member configured to be able to tilt in an optional direction;
    a first driving unit configured to drive the examination unit;
    a position control unit configured to control the first driving unit such that fine movement driving of the examination unit is performed in a case where a tilt angle of the operating member is smaller than a first angle, and coarse movement driving of the examination unit is performed in a case where the tilt angle of the operating member is equal to or greater than the first angle;
    a second driving unit configured to drive the operating member; and
    an angle control unit configured to control the second driving unit such that the tilt angle of the operating member is automatically changed to a second angle which is smaller than the first angle, in accordance with a change from the coarse movement to the fine movement.

2. The ophthalmologic apparatus according to claim 1, further comprising:
    an angle detecting unit configured to detect the tilt angle of the operating member; and
    a detecting unit configured to detect the change from the coarse movement to the fine movement, by the detected tilt angle being changed from the first angle or greater to smaller than the first angle.

3. The ophthalmologic apparatus according to claim 1, further comprising:
    an image acquiring unit configured to acquire an image of an anterior eye portion of the eye to be examined; and
    a detecting unit configured to automatically perform the coarse movement based on the acquired image, and upon the coarse movement having been completed, detect the change from the coarse movement to the fine movement.

4. The ophthalmologic apparatus according to claim 1, further comprising:
    a switch configured to transmit a signal to the angle control unit, the switch having been provided to the operating member and operating to change the coarse movement to the fine movement; and
    a detecting unit configured to detect the change from the coarse movement to the fine movement in accordance with pressing of the switch.

5. The ophthalmologic apparatus according to claim 1,
    wherein the operating member includes a moving member configured to move in a direction in which the examination unit moves, in accordance with the tilt angle of the operating member,
    wherein the second driving unit includes a driving member, and a coupler configured to couple the driving member to the moving member,
    and wherein the angle control unit controls the driving member such that the moving member moves to a position corresponding to the second angle, in accordance with the change from the coarse movement to the fine movement.

6. The ophthalmologic apparatus according to claim 1,
    wherein the operating member includes a first member having a recess and a protrusion provided to a part of the recess, and a second member which is integrally provided with the operating member and is capable of moving in correspondence with tilting of the operating member while in contact with the first member,
    wherein, in a case where the second member is in contact with the protrusion, the distance between a center of tilting of the operating member and the second member is shorter than before the second member having come into contact with the protrusion,
    wherein the second driving unit has an elastic member provided to the recess, and a pressing unit which presses the recess,
    and wherein the angle control unit compresses the elastic member in accordance with the change from the coarse movement to the fine movement so as to control the pressing unit.

7. The ophthalmologic apparatus according to claim 1, further comprising:
    a display control unit configured to display, on a display unit, a display form indicating the change of the tilt angle of the operating member to the second angle, in accordance with the change from the coarse movement to the fine movement.

8. The ophthalmologic apparatus according to claim 1, further comprising:
    a switching unit configured to switch between a state where power is transmitted to the operating member and a state where power is not transmitted to the operating member,
    wherein the angle control unit controls the switching unit in accordance with the change from the coarse movement to the fine movement, to switch from the state where power is not transmitted to the operating member to a state where power is transmitted to the operating member, so that transmission of the power to the operating member automatically changes the tilt angle of the operating member.

9. An ophthalmologic apparatus comprising:
an examination unit configured to examine an eye to be examined;
an operating member configured to be able to tilt in an optional direction;
a first driving unit configured to drive the examination unit;
a position control unit configured to control the first driving unit in accordance with a tilt angle of the operating member;
a second driving unit configured to drive the operating member; and
an angle control unit configured to control the second driving unit such that the tilt angle of the operating member is automatically changed to a second angle which is smaller than the first angle, in accordance with a change of the tilt angle of the operating member from a first angle or greater to smaller than the first angle.

10. An ophthalmologic apparatus comprising:
an examination unit configured to examine an eye to be examined;
an operating member configured to be able to tilt in an optional direction from a neutral state;
a driving unit configured to drive the examination unit;
a position control unit configured to control the driving unit such that fine movement driving of the examination unit is performed in a case where a tilt angle of the operating member is smaller than a predetermined angle, and coarse movement driving of the examination unit is performed in a case where the tilt angle of the operating member is equal to or greater than the predetermined angle; and
a changing unit configured to change the tilt angle of the operating member in a case where the tilt angle of the operating member is smaller than the predetermined angle, so that the tilt angle of the operating member is reduced.

11. A controlling method of an ophthalmologic apparatus including an examination unit configured to examine an eye to be examined and an operating member configured to be able to tilt in an optional direction, the method comprising:
controlling a first driving unit configured to drive the examination unit such that fine movement driving of the examination unit is performed in a case where a tilt angle of the operating member is smaller than a first angle, and coarse movement driving of the examination unit is performed in a case where the tilt angle of the operating member is equal to or greater than the first angle; and
controlling a second driving unit configured to drive the operating member such that the tilt angle of the operating member is automatically changed to a second angle which is smaller than the first angle, in accordance with a change from the coarse movement to the fine movement.

12. A non-transitory computer-readable storage medium storing a program for causing a computer to execute the steps in the controlling method defined in claim 11.

13. A controlling method of an ophthalmologic apparatus including an examination unit configured to examine an eye to be examined, and an operating member configured to be able to tilt in an optional direction, the method comprising:
controlling a first driving unit configured to drive the examination unit, in accordance with a tilt angle of the operating member; and
controlling a second driving unit configured to drive the operating member such that the tilt angle of the operating member is automatically changed to a second angle which is smaller than the first angle, in accordance with a change of the tilt angle of the operating member from a first angle or greater to smaller than the first angle.

14. A non-transitory computer-readable storage medium storing a program for causing a computer to execute the steps in the controlling method defined in claim 13.

15. A controlling method of an ophthalmologic apparatus including an examination unit configured to examine an eye to be examined, and an operating member configured to be able to tilt in an optional direction from a neutral state, the method comprising:
controlling a driving unit configured to drive the examination unit, such that fine movement driving of the examination unit is performed in a case where a tilt angle of the operating member is smaller than a predetermined angle, and coarse movement driving of the examination unit is performed in a case where the tilt angle of the operating member is equal to or greater than the predetermined angle; and
controlling a changing unit configured to change the tilt angle of the operating member in a case where the tilt angle of the operating member is smaller than the predetermined angle, so that the tilt angle of the operating member is reduced.

16. A non-transitory computer-readable storage medium storing a program for causing a computer to execute the steps in the controlling method defined in claim 13.

* * * * *